United States Patent [19]
Shuman

[11] Patent Number: 6,022,854
[45] Date of Patent: Feb. 8, 2000

[54] PLATELET SPECIFIC THERAPEUTIC COMPOUND AND METHOD OF TREATING

[75] Inventor: Marc A. Shuman, San Francisco, Calif.

[73] Assignee: The Regents of the University of California, Oakland, Calif.

[21] Appl. No.: 08/425,347

[22] Filed: Apr. 17, 1995

Related U.S. Application Data

[63] Continuation of application No. 08/001,740, Jan. 4, 1993, abandoned.

[51] Int. Cl.$^7$ .......................... C07K 19/00; A61K 38/17
[52] U.S. Cl. .......................... 514/12; 530/300; 530/350; 530/380; 435/215; 514/2; 424/94.63
[58] Field of Search .................................. 530/300, 350, 530/380; 435/215; 514/2, 12; 424/94.63

[56] References Cited

U.S. PATENT DOCUMENTS 5,242,810   9/1993   Maraganore et al. .................. 435/69.2

OTHER PUBLICATIONS

A. Knapp et al. "Hirudisins" J. Biol. Chem. 267(34) 24230–24234 (Dec. 1992).
C. Bode et al. "Platelet Targeted Fibrinolysis Enhances Clot Lysis and Inhibits Platelet Aggregation" Circulation 84(2) 805–813 1991 (See Embase Abstract).
F.C. Church et al. "Chimeric Antithrombin Peptide." J. Biol Chem. 266(18) 11975–11979 (Jun. 25, 1991).
R.M. Scarborough et al. "Barbourin" J. Biol. Chem. 266(15) 9359–9362 (May 25, 1991).

*Primary Examiner*—Rebecca E. Prouty
*Attorney, Agent, or Firm*—Hana Verny

[57] ABSTRACT

A therapeutic compound comprises a KGD-containing peptide, tandem repeats thereof, combinations thereof, or combinations thereof with an RGD-containing peptide or tandem repeats thereof, or peptide analogues or non-peptide organic analogues of the RGD and KGD tripeptides, and a pharmaceutical agent. A therapeutic composition comprises the compound of this invention and a pharmaceutically acceptable carrier. A polydeoxyribonucleotide comprises a DNA sequence, and a polyribonucleotide comprises an RNA sequence, encoding the compound of the invention, where the pharmaceutical agent is a peptide. A self-replicating DNA carries the polydeoxyribonucleotide described above and a transformed host cell comprises the self-replicating DNA. Therapeutic platelets are loaded with a therapeutic compound comprising a peptide comprising RGD or KGD, peptide analogues or organic analogues thereof, tandem repeats thereof, or combinations thereof, and a pharmaceutical agent operatively linked to the peptide. A method of delivering a pharmaceutical agent to a site afflicted with a disease comprises administering an effective amount of the therapeutic platelets or the therapeutic compound comprising RGD or KGD and a pharmaceutical agent. When the method is applied to preventing or countering vascular thrombosis or atherosclerosis, the pharmaceutical agent comprises an anti-thrombotic or an anti-atherosclerotic agent or active fragments thereof, respectively, and the peptide comprises an RGD or KGD peptide or, peptide analogues or organic analogues thereof, combinations thereof.

4 Claims, No Drawings

PLATELET SPECIFIC THERAPEUTIC COMPOUND AND METHOD OF TREATING

This is a continuation of application of Ser. No. 08/001,740 filed on Jan. 4, 1993 now abandoned.

This invention was developed at least partially with Government support under Grant Nos. HL-31610 and HL-33277 from the National Heart, Lung, and Blood Institute of the National Institutes of Health. The Government may have rights in this invention.

BACKGROUND OF THE INVENTION

1. Field of the Invention

This invention relates to novel therapeutic compounds comprising a peptide, peptide analogue or organic chemical analogue targeted to megakaryocytes and platelets and a pharmaceutical agent, and to therapeutic compositions, polynucleotides encoding the compound and self-replicating polynucleotides capable of expressing the compounds. The therapeutic compounds are taken up and accumulate in the megakaryocytes that later produce platelets. The compounds of the invention are useful for inhibiting or countering vascular disorders such as thrombosis or atherosclerosis.

2. Description of the Background

Often the only effective means of treatment of the acute complications of cardiovascular diseases is the intravenous injection of a therapeutic agent. In many cases, however, these agents are somewhat toxic, and in some cases, highly toxic and their generalized distribution is not desirable. In addition, the intravenous injection of non-tissue targeted agents has other drawbacks such as the premature inactivation, catabolism and/or dilution of the agents, and the resulting lagtime in the delivery of the therapeutic agent. Higher doses, as well as a higher frequency of administration are thus required, because of its generalized distribution, to ensure the delivery of an adequate amount of drug to the target tissue. This further increases the exposure of non-target tissues to the drug and its toxic effects.

Megakaryocytes are bone marrow cells that mature into platelets. Megakaryocytes have α-granules that can accumulate some exogenous compounds such as fibrinogen. When megakaryocytes differentiate into platelets, the α-granules are dispersed into the maturing platelets. When deleterious events, such as injury or disease, occur within the circulatory system, they trigger the mobilization of platelets to the site of vascular damage. At the site of injury, the platelets are activated, e.g., to prevent blood loss through platelet aggregation and to release proteins active in coagulation. It is widely accepted nowadays that megakaryocytes do not synthesize the fibrinogen present in α-granules, but rather, acquire this protein by endocytosis. In addition to fibrinogen, the α-granules also contain, for example, platelet factor 4 (PF-4), and other proteins such as immunoglobulin G and albumin. The endocytosis of fibrinogen by megakaryocytes and platelets is thought to be mediated by the $\alpha_{IIb}\beta_3$ receptor, that is part of a family of cell surface receptors known as integrins. Platelets, and presumably megakaryocytes, also contain several other integrins, including receptors for vitronectin ($\alpha_v\beta_3$), collagen ($\alpha_2\beta_1$), fibronectin ($\alpha 5\beta 1$), and laminin (VLA-6). The vitronectin receptors, $\alpha_v\beta_3$, although present in low numbers, also bind fibrinogen.

Most cells synthesize their own proteins and store them in secretory granules. A few cell types such as basophilic leukocytes, mast cells, granule-containing lymphocytes, salivary gland cells, and megakaryocytes also incorporate exogenous proteins into their granules by endocytosis. However, little is known about the mechanisms and pathways involved in the uptake and incorporation of these exogenous proteins into the granules. The coated pit-mediated internalization of the LDL receptor was recently shown to require the presence of the consensus sequence NPXY, where X stands for any amino acid. The NPXY sequence was also found in cytoplasmic domains of some integrin subunits, including GP IIIa of platelets.

Fibrinogen constitutes ten percent of α-granule proteins and is the predominant adhesive protein secreted by platelets. Recent data indicate that fibrinogen is not synthesized by the bone marrow megakaryocytes, as previously thought, but is acquired exclusively from plasma by endocytosis. Because fibrinogen is present in the α-granules at a higher concentration than other proteins acquired exclusively from plasma, i.e., albumin, the endocytosis of fibrinogen is likely to be receptor-mediated. A variety of ligands, including fibrinogen, vWf, fibronectin, and thrombospondin, bind to the $\alpha_{IIb}\beta_3$ receptor on stimulated platelets. The recognition sequence common to these proteins is RGD. The fibrinogen molecule contains two RGD sequences both on the Aα chain. Fibrinogen also contains an additional $\alpha_{IIb}\beta_3$ binding site located at the C-terminus of the γ chain, which includes 12 amino acids but does not contain the RGD sequence. This dodecapeptide and the RGD-containing peptides compete with each other for binding to the $\alpha_{IIb}\beta_3$ receptor.

Attempts have been made to target drugs to specific tissues, such as cancer cells, for improved drug therapy (U.S. Pat. No. 5,135,736 to Anderson et al.). These cytotoxic agents designed to specifically bind target cells, however, may still need to be administered intravenously.

The administration of therapeutic agents for the treatment of cardiovascular diseases is often affected by the above described deficiencies, despite the intimate association of the circulatory system with the target tissue.

Accordingly, there is still a need for an improved therapeutic compound to more effectively treat cardiovascular diseases such as coronary thrombosis and atherosclerosis, which is specifically targeted for delivery to the diseased site and, therefore, produces minimal side effects.

SUMMARY OF THE INVENTION

This invention relates to a therapeutic compound comprising a peptide comprising KGD, peptide analogues or organic molecule analogues of KGD or RGD, tandem repeats thereof, combinations thereof, combinations thereof with a peptide comprising RGD or tandem repeats thereof, and a pharmaceutical agent operatively linked to the peptide.

This invention also relates to a therapeutic composition comprising the compound of this invention, and a pharmaceutically-acceptable carrier.

Also part of this invention is a polydeoxyribonucleotide comprising a DNA sequence, and a polyribonucleotide comprising an RNA sequence, encoding the compound of the invention, wherein the pharmaceutical agent is a pharmaceutical peptide.

This invention also relates to a self-replicating DNA, having the polydeoxyribonucleotide of this invention operatively linked thereto and a transformed host cell comprising the self-replicating DNA described above.

Also part of this invention are therapeutic platelets and megakaryocytes comprising a peptide comprising RGD or KGD, peptide analogues or organic molecules analogues of RGD or KGD, tandem repeats thereof, or combinations thereof, and a pharmaceutical agent operably linked to the peptide or analogue.

This invention also encompasses a method of delivering a pharmaceutical agent to a site that is injured or afflicted with a disease that triggers the mobilization of platelets to the site by administering an effective amount of a therapeutic compound comprising an RGD or KGD peptide segment or peptide or organic analogues of RGD or KGD, and a pharmaceutical agent, allowing the therapeutic compound to reach and be taken up by megakaryocytes and platelets, and allowing the platelets, when mobilized to the injured or disease site, to deliver the therapeutic agent to the site, where it exerts its effect. This method may also be practiced by administering platelets loaded with the therapeutic compound. When the method is applied to preventing or countering vascular thrombosis, the pharmaceutical agent may comprise an anti-thrombotic agent, and when the method is applied to preventing or countering atherosclerosis, the pharmaceutical agent may comprise an anti-atherosclerotic agent.

Other objects, advantages and features of the present invention will become apparent to those skilled in the art from the following discussion.

DESCRIPTION OF THE PREFERRED EMBODIMENTS

This invention arose from a desire by the inventor to provide targeted therapeutic compounds and methods for treating diseases that mobilize platelets to specific sites of disease, such as is the case in vascular thrombosis and atherosclerosis. The inventor has constructed novel therapeutic compounds targeted to megakaryocytes and/or platelets. These therapeutic compounds are taken up and transported by the platelets, when the latter are summoned up to the diseased site, and are then unloaded at that site. The therapeutic compounds of this invention are constructed to contain a pharmaceutical agent capable of inhibiting or countering conditions that involve the mobilization of platelets, such as thrombosis or atherosclerosis. Pharmaceutical agents of various kinds may thus be delivered by the platelets to the diseased sites.

In accordance with this invention, megakaryocytes and platelets can be loaded with the therapeutic compounds of this invention either in vitro or in vivo. When the platelets containing these therapeutic compounds are activated, they travel to the site of vascular damage and release the therapeutic compound, thus making the pharmaceutical agent available at the site of injury.

The inventor has found that megakaryocyte receptors specifically bind snake venom proteins known as "disintegrins". Both disintegrins and natural ligands such as fibrinogen possess specific Arg-Gly-Asp (RGD) or Lys-Gly-Asp (KGD) tripeptide sequences, through which they specifically bind to the $\alpha_{IIb}\beta_3$ receptor of megakaryocytes and platelets. The KGD peptide sequence binds with unexpectedly high affinity to megakaryocytes.

The present inventor hypothesized that if $\alpha_{IIb}\beta_3$ and/or $\alpha_v\beta_3$ are the receptor(s) that mediate fibrinogen uptake, an antagonist of these receptors, such as kistrin, might inhibit fibrinogen endocytosis, and even be taken up by the cells. Kistrin is a viper venom of the disintegrin family, that contains the Arg-Gly-Asp (RGD) sequence, and binds with high affinity to the $\alpha_{IIb}\beta_3$ platelet receptor. Other disintegrins, such as barbourin, contain the Lys-Gly-Asp (KGD) sequence. Kistrin's inhibition of the binding of the purified platelet $\alpha_{IIb}\beta_3$ receptor to immobilized fibrinogen is about 100 times greater than that by a peptide with the Gly-Arg-Gly-Asp-Ser sequence. Furthermore, kistrin was shown to bind to $\alpha_{IIb}\beta_3$ and to reversibly inhibit platelet aggregation in vivo without inducing thrombocytopenia. Bound kistrin was subsequently deposited in platelet granules.

This invention provides a therapeutic compound comprising a peptide comprising KGD, peptide analogues or organic molecule analogues of RGD or KGD, tandem repeats thereof, combinations thereof, combinations thereof with a peptide comprising RGD or tandem repeats thereof, and a pharmaceutical agent operatively linked to the peptide.

Any peptide sequence is suitable for use herein as long as it contains the KGD tripeptide, peptide analogues thereof or organic molecule analogues of KGD or RGD, that provides the highest platelet-specific targeting capability. The peptide portion of the therapeutic compound may be prepared by recombinant technology starting from a DNA segment encoding the desired peptide sequence, cloning and transfection of a eukaryotic or prokaryotic cell as is known in the art. When the DNA does not encode the KGD tripeptide, it may be modified with proper primers by polymerase chain reaction amplification as is known in the art. In addition, the peptide or peptide analogue of the present invention may be prepared by direct synthesis as is also known in the art. Peptide-organic molecule hybrids may be prepared by synthesis as is known in the art. Typically, the organic molecule will have a reactive group such as carboxyl, amino, hydroxyl, halogen, maleimido, and sulphydryl, among others. The peptides utilized herein may contain any number of amino acids, and preferably about 3 to 10,000 amino acids, and more preferably about 150 to 2500 amino acids. Within the sequence of the peptide there may be one or more KGD tripeptides, one or more RGD tripeptides, one or more peptide analogues, one or more organic molecule analogues, or one or more KGD tripeptides and one or more RGD tripeptides. These sequences may also contain tandem repeats of the KGD tripeptide, combinations thereof and combination thereof with the RGD tripeptides. These different variants of the peptides may preferably be prepared by recombinant technology. Once the DNA fragments encoding a desired peptide are synthesized, several of them may be ligated to one another to form tandem repeats of the entire sequence, or tandem repeats of the nucleotide sequence encoding KGD tripeptide can be operatively linked to the rest of the DNA.

The molecules may also be peptide analogues in which one or more amino acids of the peptide are substituted by one or more unnatural or natural amino acid analogues. They may also be non-peptide organic molecules which mimic the spacial distribution of the KGD and RGD sequences.

In one preferred embodiment, the peptide of the invention comprises a disintegrin selected from the group consisting of barbourin, kistrin, echistatin, eristicaphin, tergeminin and trigamin, among others, wherein K is substituted for R in the RGD sequence, and fragments thereof comprising KGD. Barbourin itself contains the KGD tripeptide sequence, whereas the remaining disintegrins contain the RGD sequence and therefore a K must be substituted for R. This may be done at the DNA level by mutation of the codon for this amino acid as is shown in the exemplary disclosure provided herein. In one preferred embodiment, the compound comprises a KGD peptide of about 50 to 85 amino acids and an anti-thrombotic drug or fragment thereof attached hereto. In another preferred embodiment, the peptide of the invention comprises echistatin, wherein K is substituted for R in the RGD sequence or a fragment thereof comprising KGD, and urokinase or an active fragment thereof operatively linked thereto. In this particular embodiment, the therapeutic compound of the invention comprises a hybrid protein of about 20 to 15,000 amino acids, preferably about 150 to 2,500 amino acids, and more preferably of about 360 to 400 amino acids. However, smaller fragments or larger fragments, and those having additional bridging amino acid sequences, may also be utilized. The technology for manufacturing hybrid proteins is also known in the art and need not be further described herein. Moreover, the targeting peptide may be altered to eliminate sequences so as to, for example, minimize unwanted side effects.

The tripeptide sequence arginine-glycine-aspartic acid (Arg-Gly-Asp; RGD) on fibrinogen as the binding site for GPIIb-IIIa has led to alternative sequences that are potent antagonists of the fibrinogen receptor GPIIb-IIIa. While the linear peptide RGD inhibits fibrinogen binding and platelet aggregation, the affinity for GPIIb-IIIa is low. The potency is dramatically improved by cyclization of the RGD sequence, most often by flanking RGD with sulfur containing residues and subsequent cyclization via a disulfide bridge. This approach is typified in a series of peptides shown below, which are known in the art.

---

Ac-Arg-Gly-Asp-Ser-NH₂
Ac-Cys-Arg-Gly-Asp-Cys-NH₂
Ac-Cys-Arg-Gly-Asp-Pen-NH₂
Ac-Cys O-Arg Gly Asp Pen NH₂
Ac-Cys-(N-Me)Arg-Gly-Asp-Pen-NH₂
Ac-Cys-Asn-Dtc-Arg-Gly-Asp-Cys-OH
AC Cys-Asn-Dtc-Amf-Gly-Asp-Cys-OH

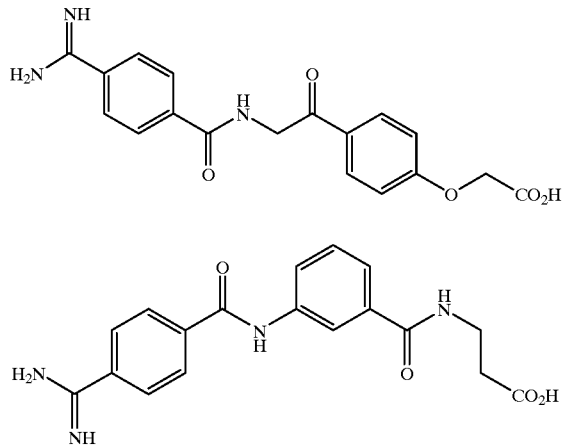

---

Examples of peptides analogues of the RGD and/or KGD peptides are known in the art. Some of these are described by Barker, P. L., et al. and McDowell, R. S., et al. (Barker et al., "Cyclic RGD Peptide Analogs as Anti-Platelet Antithrombotics", J. Med. Chem. 35:2040–2048 (1992); McDowell and Gadek, "Structural Studies of Potent Constrained RGD Peptide", J. Amer. Chem. Soc. 114:9245–9253 (1992)), the relevant part of the text is incorporated herein by reference.

A peptide/organic molecule hybrid analogue suitable for use herein is known in the art as in the following structure

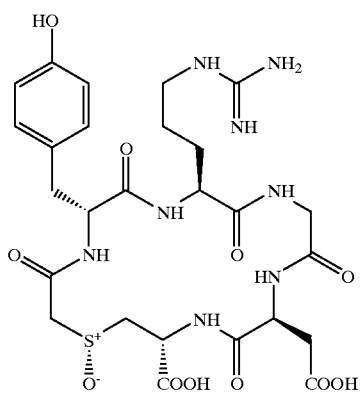

A large number of other analogues are also listed in the above cited references.

Non-peptide, organic molecule analogues are also known in the art and are described, for instance, by Hartman et al., Alig et al., EPO Patent Application to Searle, Samanen et al. and Callahan et al. (Hartman, G. D., et al., "Non-Peptide Fibrinogen Receptor Antagonists. 1. Discovery and Design of Exosite Inhibitors", J. Med. Chem., 35:4640–4642 (1992); Alig, L. et al., "Low Molecular Weight, Non-Peptide Fibrinogen Receptor Antagonist", J. Med. Chem. 35:4393–4407 (1992); EP 0 502 536 to Searle, G. D.; Samamen, J., et al., "A Development of a Small RGD Peptide Fibrinogen Receptor Antagonist with Potent Anti-aggregatory Activity In Vitro", J. Med. Chem 34:3114–3125 (1991); and Callahan, J. F., et al., "Design and Synthesis of a C₇ Mimetic for the Predicted γ-Turn Conformation Found in Several Constrained RGD Antagonists", J. Med. Chem. 35:3970–3972 (1992)), the relevant part of the text is incorporated herein by reference.

Examples of these are shown below.

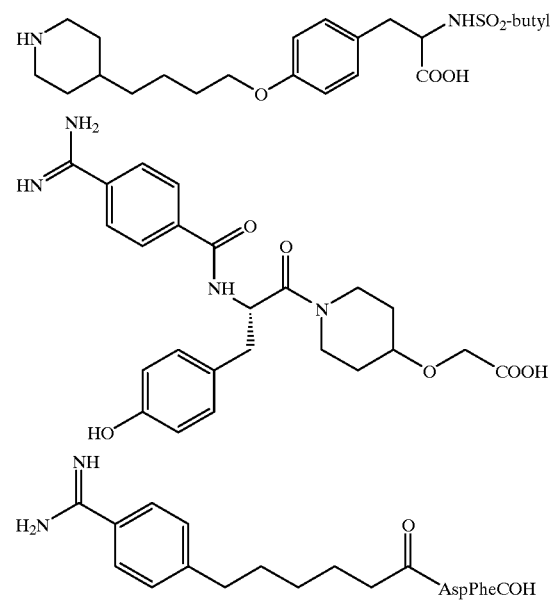

The pharmaceutical agent may comprise compounds or active fragments thereof that are effective to treat any diseases that summon platelets to the site of injury. One such disease, vascular thrombosis, is currently treated by either inhibiting thrombogenesis or by fibrinolysis of cross-linked fibrin after clot formation, as is known in the art. Clearly, any pharmaceutical agent that, upon being loaded into megakaryocytes and/or platelets and being delivered at the site of disease, may be of therapeutic help to a patient and may be utilized herein. Thus, the pharmaceutical agent may be selected from anti-thrombotic agents in general, and particularly urokinase, tissue plasminogen activator, hirudin, and heparin, or active fragments thereof, among others. However, other anti-thrombotic agents may also be utilized, such as small anti-thrombotic non-peptide molecules.

Other pharmaceutical agents effective in preventing cardiovascular diseases may also be used. Such agents may act by stimulating the repair of the vascular endothelium, such as vascular endothelial cell growth factors including vascular endothelial cell growth factor or platelet derived endothelial growth factor, or by inhibiting the development of atherosclerotic plaque or oxidative damage. Multiple pharmaceutical agents or multiple peptides of the same agent may be incorporated into the same therapeutic compound.

In another embodiment, the pharmaceutical agent comprises an anti-atherosclerotic agent, such as an inhibitor of platelet-derived growth factor, an inhibitor of monocyte chemotaxis factor, endothelial growth factors, or an anti-oxidant such as superoxide dismutase, or active fragments thereof, among others. However, other types of anti-atherosclerotic agents may also be utilized herein, such as the organic molecules referred to above.

A variety of anti-thrombotic agents are known in the art and has been used for the therapy of cardiovascular diseases. A large number of them and their categories are described by Jakubowski et al. (Jakubowski, J. A., et al., "Future Anti-thrombotic Therapy", Annu. Rep. Med. Chem. 27:99–108 (1992)), the relevant text of which is incorporated herein by reference.

When the pharmaceutical agent comprises an anti-thrombotic or anti-atherosclerotic agent, the peptide may comprise either an RGD or a KGD tripeptide, peptide analogue or non-peptide organic molecule analogue thereof, tandem repeats or combinations thereof or fragments thereof, or peptide analogues or organic analogues of the RGD or KGD sequence.

The therapeutic compound may also comprise an additional, possibly a bridging peptide sequence, e.g., to facilitate the purification of the therapeutic compound. The additional peptide may comprise, for example, a binding site for affinity chromatography purification or an antigen capable of binding to a monoclonal antibody. The bridging peptide may be intercalated simply to facilitate the preparation of the compound.

An RGD-containing targeting peptide may be modified to convert the less efficient binding RGD to the more highly binding KGD tripeptide sequence or related peptide analogue or organic analogue thereof. In addition, other neighboring amino acids may also be modified to enhance the binding of the KGD tripeptide to megakaryocyte or platelet receptors. In addition, multiple binding KGD and/or RGD sequences or analogues thereof may be incorporated to maximize the binding of the compound to megakaryocyte integrin receptors and its endocytosis.

The therapeutic compound of the invention is also provided as a therapeutic composition that further comprises a pharmaceutically-acceptable carrier. All the compounds described above are suitable for use in the composition of the invention. Pharmaceutically-acceptable carriers are known in the art and will not be described herein in great detail. These carriers may be liquid or solid, or they may be presented as an aerosol. Preferred are liquid carriers. Pharmaceutically-acceptable carriers as utilized in the context of this patent include any and all solvents, dispersing media, surfactants, compounds suitable to maintaining physiological osmolarity, pH and isotonicity, anti-microbial agents, absorption delaying agents and the like, as is known in the art. Typically, the pharmaceutically-acceptable carrier is also non-proteolytic so that the peptide portion of the therapeutic compound is not hydrolyzed prior to administration.

The therapeutic compound of the invention may be broadly present in the composition. Typically, an amount of the compound of about 0.1 to 99.9 wt %, and more preferably about 1 to 25 wt %, of the composition is suitable. However, other amounts are also possible. The composition may be prepared in dosage unit form, for uniform dosage and administration. Each dosage unit contains a predetermined quantity of active ingredient calculated to produce a desired therapeutic effect in association with a required amount of pharmaceutical carrier. The composition may also be provided in bulk.

The composition of the invention may be prepared by admixing the ingredients as is known in the art. The therapeutic compound and the carrier may be comminuted and compounded as is known in the art. Other ingredients may also be added as is known in the art. Particular care must be exercised not to alter the integrity of any of the ingredients.

When the pharmaceutical agent itself is a peptide, this invention also provides a polydeoxyribonucleotide comprising a DNA segment encoding the therapeutic compound described above, wherein the DNA encoding the pharmaceutical agent is operatively linked to the KGD or RGD-encoding DNA sequence. The DNA segment must encode the KGD or RGD tripeptides at least once. When the therapeutic compound is to contain combinations of the tripeptides or tandem repeats thereof, the polydeoxyribonucleotide may be designed to contain the corresponding codons in the desired places. Additional DNA sequences, other than those encoding the targeting peptide and the therapeutic agent, may also be operatively linked thereto, as desired. The additional DNA sequence may encode an amino acid sequence effective to purify the therapeutic compound.

Where the therapeutic agent is a peptide, this invention also provides a polyribonucleotide comprising an RNA sequence encoding the therapeutic compound, where a DNA segment encoding the therapeutic agent is operatively linked to the DNA segment encoding the targeting peptide. The DNA and RNA sequences of this invention may be prepared by methods known in the art. Typically, either starting from DNA and/or RNA sequences encoding existing gene products and modifying them with predesigned primers by PCR amplification, or by synthesizing the nucleotide segments by methods known in the art.

Also provided herein is a self-replicating DNA having the polydeoxyribonucleotide of the invention operatively linked thereto. The self-replicating DNA may be any DNA sequence that contains the necessary polynucleotides for self-replication, and optionally transcription and translation. In one embodiment, the self-replicating DNA is a vector and the vector has the polydeoxyribonucleotide encoding the therapeutic compound operatively linked thereto. The above vector is preferably an expression vector so that the polydeoxyribonucleotide may be expressed in a host cell in vitro or in vivo.

Also encompassed by this invention is a transformed host cell comprising the self-replicating DNA carrying the polynucleotide of the invention. The host cell may be transfected with the hybrid vector by methods known in the art, and the therapeutic compound expressed therein. The host cells may be prokaryotic or eukaryotic cells.

This invention also provides therapeutic megakaryocytes and/or platelets loaded with the therapeutic compound of this invention. The compound may comprise a peptide comprising an RGD or KGD tripeptide, tandem repeats thereof or combinations thereof, or peptide or organic molecule analogue of RGD/KGD and a pharmaceutical agent operatively linked to the peptide such as is described above. The platelets may be prepared by administering the therapeutic compound to a subject. After a suitable period effective to load a desired amount of the compound into the platelets, the latter may be harvested and stored as is known in the art. Alternatively, platelets and/or megakaryocytes may be obtained from a donor and loaded in vitro by contact with the composition of the invention for a suitable period of time. The platelets or megakaryocytes are preferably obtained from a patient for self-infusion and loaded with the therapeutic compound in vitro. Megakaryocytes may be loaded in vitro and allowed to differentiate into platelets prior to their utilization. Presently, hospitals have platelet supplies that may be loaded with a desired therapeutic compound prior to administration. The storage of loaded platelets will permit the rapid implementation of the therapeutic platelets to meet clinical demands. Megakaryocytes may also be stored for loading and differentiation into platelets prior to their use.

The therapeutic agent may be delivered to a site afflicted with a disease that triggers the mobilization of platelets in accordance with this invention. In one embodiment, the method provided herein comprises the administration of an effective amount of a therapeutic compound comprising a peptide, peptide analogues and organic analogues comprising either a KGD or RGD tripeptide or both, or analogues thereof and a therapeutic agent operatively linked thereto, allowing the therapeutic compound to reach, and be taken up by, megakaryocytes or platelets, and allowing the platelets, when mobilized to the disease site, to deliver the therapeutic agent to the site, and the agent to exercise its therapeutic effect. In some instances, the triggering condition that mobilizes the platelets is the exposure of subendothelial structures such as collagen. The therapeutic compound may also be administered as the therapeutic platelets of this invention.

The inclusion in the targeting peptide of more than one KGD or RGD segments, tandem repeats thereof or combinations thereof, or analogues of these sequences enhances its effectiveness by promoting greater binding to megakaryocyte or platelet receptors, and its uptake and concentration in these cells. Because the therapeutic compound specifically binds to megakaryocytes and/or platelets and is thereby removed from circulation, it is possible to administer it at a low dose that is sufficient to saturate the megakaryocyte and/or platelet pool, with a minimal amount remaining in circulation. The administration of a low dose together with the rapid uptake of the compound by megakaryocytes and/or platelets minimizes any inherent side-effects of the pharmaceutical agent since less of the agent is in contact with other tissues.

The method of the invention may be applied to preventing or countering vascular thrombosis by administration of an effective amount of a therapeutic compound comprising an RGD- or KGD-containing peptide, peptide analogues or organic analogues thereof, and an anti-thrombotic agent operatively linked thereto. The anti-thrombotic agent is typically a compound capable of inhibiting thrombogenesis and/or promoting fibrinolysis as described above. Suitable anti-thrombotic agents are anticoagulants such as hirudin, heparin, fibrinolytic agents such as tissue plasminogen activator and urokinase, and active fragments thereof. However, others are also suitable, such as small organic molecules.

The method of the invention may also be applied to preventing or countering atherosclerosis by administering to a subject in need of the treatment a composition comprising an effective amount of a therapeutic compound comprising an RGD- or KGD-containing peptide, tandem repeats thereof or combinations thereof, peptide analogue or organic analogues thereof, and a pharmaceutical agent comprising an anti-atherosclerotic agent operatively linked thereto. The pharmaceutical agent may comprise inhibitors of platelet-derived growth factor, inhibitors of monocyte chemotaxic factor, endothelial growth factors, anti-oxidants and inhibitors of coagulation and active fragments thereof, among others, including small organic molecules.

The therapeutic compound may be administered in an amount of about 0.001 to 100 mg/kg body weight/dose, and more preferably about 0.01 to 10 mg/kg body weight/dose. A suitable daily dose is about 1 to 100 mg/kg body weight. However, other amounts may also be administered.

The administration of the therapeutic compound of the invention may be undertaken by various routes. Preferred is by injection but as long as the peptide bonds are protected in the formulation, other routes such as the oral route are also suitable.

Having now generally described this invention, the same will be better understood by reference to certain specific examples, which are included herein for purposes of illustration only and are not intended to be limiting of the invention or any embodiment thereof, unless so specified.

EXAMPLES

Example 1: Materials

Grade L human fibrinogen was used in all examples (KabiVitrum, Stockholm, Sweden). Kistrin was prepared as previously described (Dennis, M. S., et al., "Platelet Glycoprotein IIb-IIIa Protein Antagonists from Snake Venoms: Evidence for a Family of Platelet-Aggregation Inhibitors", P.N.A.S. (USA) 87:2471–2475 (1989)).

The antibodies used include rabbit anti-guinea pig albumin (Cappel, Organon Teknika Corp., Rockville, Md.), rabbit anti-human vWf (Dako Corp., Carpinteria, Calif.), rabbit anti-biotin (Enzo Biochem. Inc., New York, N.Y.), and anti-human PF-4 (obtained from Dr. Shirley Levine, San Antonio, Tex. These antibodies, prepared against human proteins, cross-react with their guinea pig counter-parts.

The biotinylated goat anti-rabbit IgG antibody was purchased from Vector Labs Inc., Burlingame, Calif. and the 1 nm gold-conjugated goat anti-rabbit IgG from Amersham Corp., Arlington Heights, Ill. The streptavidin-conjugated peroxidase and biotinylated peroxidase were purchased from Zymed Labs., San Francisco. The blocking reagents for endogenous tissue biotin consisting of avidin-D and biotin were obtained from Vector Labs.

The snake venom peptides kistrin and barbourin were obtained from Genentech Inc. and COR Therapeutics, respectively. The amino acid sequences of barbourin and kistrin are known (Scarborough, R. M., et al., J.Biol. Chem. 266:9359 (1 991); Adler, M. et al., Science 253:445 (1991)).

Example 2: Biotinylation of Fibrinogen

Purified fibrinogen was biotinylated according to a previously described method (Handagama, P. J., et al., "Incorporation of Intravenously Injected Albumin, Immunoglobulin G and Fibrinogen in Guinea Pig Megakaryocyte Granules", J. Clin. Invest. 84:73–82 (1989)). This biotinylated fibrinogen migrated as the intact protein on Western immunoblots of SDS gels. No biotinylated degradation products were detected.

Example 3: Biotinylation of Kistrin 5.0 mg kistrin, 2.5 mg/ml in 0.15 M NaCl/0.01 M NaPO$_4$, pH 7.4, were incubated with biotinyl-ε-amino-caproic acid N-hydroxysuccinimide ester at a final concentration of 50 µg/ml at 0° C. for 3 hrs. The biotinylated kistrin was then dialyzed extensively against 0.15 M NaCl/0.01 M NaPO4, pH 7.4, using low molecular weight cutoff (1000 MW) dialysis tubing from SPECTRA/POR.

Example 4: In Vivo Endocytosis Blocking Effect of Kistrin in Megakaryocytes

Ten male Hartley guinea pigs, each weighing 450–500 g, were used. Because kistrin appears to have a short in vivo half life, it was administered by slow, continuous, intravenous infusion (Dennis et al. (1989), supra). This maintained a sustained kistrin level in blood and, therefore, a continuous blockade of the receptors. All substances were administered to guinea pigs via an in-dwelling jugular catheter. Continuous infusions were provided using a compact infusion pump.

To determine the blocking effect of kistrin on megakaryocyte receptors, the animals were given 200 µg kistrin in saline/hr by continuous intravenous infusion for 1 hr., followed by a bolus of 250 mg biotinylated fibrinogen. The infusion of kistrin at 200 mg/hr was then continued for 24 hrs.

Control animals received a similar volume of saline in place of kistrin, followed by the biotinylated fibrinogen. The animals were sacrificed 24 hrs. later, and the bone marrow and blood platelets processed for immunohistochemical detection of biotinylated fibrinogen.

Example 5: Fate of Kistrin in Megakaryocytes and Platelets

A separate group of experiments were conducted to determine the fate of kistrin bound in vivo to megakaryocytes and platelets. In these experiments biotinylated kistrin was infused into guinea pigs over a 4 hr. period. The localization of biotinylated kistrin in megakaryocytes was determined on plastic embedded bone marrow sections prepared for light microscopy. The kistrin present in platelets was localized by frozen thin section electron microscopy as described below.

Example 6: Uptake of Protein by Megakaryocytes

After the animals were sacrificed, the bone marrow was perfusion-fixed (4% paraformaldehyde in 0.1 M phosphate buffer, pH 7.4, for 4 hrs. at 4° C.), embedded in plastic (JB 4, Polysciences, Inc., Warrington, Pa.), and processed for immunohistochemistry as described previously (Handagama et al. (1989), supra).

The localization of albumin, vWf, and PF-4 in bone marrow megakaryocytes was carried out using previously described immunohistochemical staining techniques (Handagama et al. (1989), supra), except that the biotin-sites in the tissue (injected biotinylated protein) were blocked using a biotin-blocking kit prior to applying the primary antibodies.

To determine the specificity of staining for biotin, bone marrow sections were preincubated with biotin-blocking reagents, followed by the histochemical protocol for the biotin-specific reagents.

In another control, staining marrow from an untreated guinea pig was stained for the presence of biotin. Controls for immuno-histochemistry included the substitution of non-immune rabbit serum for the primary antibody.

Example 7: Platelet Aggregation and Platelet Counting

Platelet aggregation was quantitated using a whole blood aggregometer (model 560 VS, Chrono-Log Corp., Havertown, Pa.), with collagen as the agonist. Blood was collected by cardiac puncture into 3.8% sodium citrate. The activity of kistrin in the guinea pig was determined by inhibition of normal guinea pig platelet aggregation in vitro with kistrin. The aggregation assays were performed using blood drawn from animals continuously infused with kistrin, barbourin or saline (control) at 24 hrs.

Platelet counting was performed on samples prior to 6 hrs. and 24 hrs. after kistrin or barbourin treatment using a Coulter counter (Coulter Corp., Hialiah, Fla.).

Example 8: Detection of Biotinylated Fibrinogen in Platelets

Blood was collected from the animals 24 hrs. after biotinylated-fibrinogen infusion of kistrin-treated and control animals. The platelets were harvested, washed, and solubilized in 2.0% sodium dodecyl sulfate (SDS) as previously described (Handagama et al. (1989), supra). The solubilized platelets were electrophoresed in non-reduced 5% SDS polyacrylamide gels at 100 V. The protein bands were transferred to 0.45 mm nitrocellulose, by Western blotting by incubation for 1 hr. at 100 V, blocking for 30 minutes with 5% gelatin, incubation with avidin-horseradish peroxidase diluted 1:500 for 1 hr., and washing 3 times with Tris-buffered saline, pH 7.4. The reaction was terminated with 4-chloronapthol and hydrogen peroxide.

To determine the sensitivity of the Western blotting technique, a dilution series of biotinylated fibrinogen was electrophoresed in a 5% SDS polyacrylamide gel, transferred to nitrocellulose, and stained with avidin-peroxidase as described above.

Example 9: Detection of Other α-Granule Proteins in Platelets

The effect of kistrin on two other α-granule proteins was determined using immunoblots. The presence of the PF-4 and vWf proteins was shown by immunochemical staining using antigen specific rabbit antibodies. Platelet α-granule albumin was quantitated by radial immunodiffusion (RID), using a commercially available immunoplate for measuring low levels of albumin (NANORID Albumin LL, The binding site Inc., San Diego, Calif.). Although the antibody used in the assay was prepared against human albumin, it cross-reacted with its guinea pig counterpart with comparable avidity.

The protein from washed guinea pig platelets was prepared as for Western blots. $2 \times 10^7$ platelets were solubilized in 1% Triton X-100 in PBS, and freeze-thawed and sonicated for 15 minutes. The protein from the $2 \times 10^7$ platelets was electrophoresed in unreduced 18% SDS polyacrylamide gels at 100 V, and transferred at 100 V for 1 hr. to 0.1 mm nitrocellulose. Rabbit anti-human PF-4 antibody, diluted 1:100 in 1 % gelatin was incubated with the filter for 1 hr. at room temperature (~20° C.). The filters were washed, incubated with goat anti-rabbit IgG conjugated to biotin 1:500 for 1 hr., washed, then incubated with avidin-horseradish peroxidase (1:500) for 30 minutes, and washed. The reaction was terminated with 4-chloronapthol and $H_2O_2$.

The protein from the $2 \times 10^7$ platelets was electrophoresed in reduced 5% SDS polyacrylamide gels at 100 V for 1 hr., transferred to 0.45 mm nitrocellulose at 100 V for 1 hr., and then incubated with rabbit anti-human vWf antibody diluted 1:500 in 1 % gelatin for 1 hrs. Three dilutions of purified guinea pig albumin (Sigma) were used to obtain a standard curve from which the protein content of the blood was determined.

Example 10: Electronmicroscopic Localization of Kistrin in Platelets

This experiment was conducted to determine if kistrin molecules were endocytosed by platelets. Biotinylated kistrin was injected and localized by electron microscopy on frozen thin sections. Platelets were fixed in 4% paraformaldehyde in 0.1 M phosphate buffer, pH 7.4, for 2 hrs. at 4° C., then infiltrated overnight with 2.3 M sucrose, embedded in sucrose, frozen, and stored in liquid nitrogen, and thin sections prepared. The biotinylated kistrin was localized using rabbit anti-biotin antibody and a 1 nm gold probe conjugated to goat anti-rabbit IgG. The small probe was then amplified using silver chloride to facilitate detection (Stierhof, Y. D., et al., "Suitability of Different Silver Enhancement Methods Applied to 1 nm Colloidal Gold Particles: An Immunoelectron Microscopic Study", J. Elec. Micro. Tech. 17:336–343 (1991)). Controls consisting of platelets from normal guinea pigs were prepared and stained identically.

Example 11: Effect of Kistrin on Endocytosis of Fibrinogen by Megakaryocytes When biotinylated fibrinogen is administered to guinea pigs, it is endocytosed by bone marrow megakaryocytes and incorporated into α-granules (Handagama et al. (1 989), supra).

Guinea pigs were injected with biotinylated fibrinogen, and their bone marrows embedded in plastic and stained for biotinylated fibrinogen using streptavidin-horseradish peroxidase and counterstained with hematoxylin. The injected biotinylated fibrinogen was endocytosed by bone marrow megakaryocytes in control animals as shown by the presence of brown peroxidase reaction product at antigenic sites. In addition, the presence of biotinylated fibrinogen in the bone marrow vasculature demonstrated that labeled fibrinogen was still circulating at the time of sacrifice.

In contrast, when biotinylated fibrinogen was injected i.v. into animals given kistrin, there was a marked diminution, often to the extent of complete absence, of staining in bone marrow megakaryocytes.

A quantitative analysis of these data are presented in Table 1 below.

TABLE 1

Quantitation of Biotinylated Fibrinogen in a Pig Bone Marrow Megakaryocytes

| Biotinylated Fibrinogen | % Megakaryocytes Showing Staining | | |
|---|---|---|---|
| | None | Faint | Heavy |
| Kistrin | 60 | 40 | 0 |
| Saline | 2 | 25 | 73 |

% of total recognizable megakaryocytes in marrow derived from analysis of 200 megakaryocyte profiles under oil immersion.

The megakaryocytes were found to lack labeled fibrinogen. However, sinusoids indicate the presence of biotinylated fibrinogen in the circulation. Although kistrin-treated megakaryocytes lacked biotinylated fibrinogen, marrow sinusoids of the same animals contained labeled fibrinogen at levels comparable to controls.

When a guinea pig received a continuous infusion of kistrin for the duration of the experiment, and the bone marrow was obtained 24 hrs. after a bolus injection of biotinylated fibrinogen, the megakaryocytes did not contain labeled fibrinogen. The staining of sinus endothelial cells indicate the presence of biotinylated fibrinogen in the circulation (Photomicrographs not shown). This result indicates that even though fibrinogen was circulating and available to megakaryocytes and platelets, it was not endocytosed in the presence of kistrin. However, the staining of megakaryocytes for two other α-granule proteins, known to be synthesized endogenously, vWf and PF-4, showed no difference between treated and control animals.

Controls were run to confirm the specificity of staining bone marrow sections by preincubating with biotin-blocking reagents. No staining was seen with streptavidin-peroxidase reagents. This confirms the specificity of the staining procedure. Furthermore, bone marrow from untreated guinea pigs also lacked biotin-specific staining. Moreover, the substitution of non-immune serum for the primary antibody resulted in absence of all staining.

To determine the cellular location of kistrin, bone marrow from animals treated with biotinylated kistrin was prepared for microscopy.

When bone marrow from animals given biotinylated kistrin was stained with streptavidin-horseradish peroxidase, labeled protein was observed within the megakaryocytes (Not shown).

Example 12: Effect of Kistrin on Platelet Aggregation

When kistrin was infused into a guinea pig and the platelets extracted, it was observed that the in vitro collagen-induced platelet aggregation was inhibited in a dose-dependent manner. The platelets obtained from a control animal given a saline infusion aggregated rapidly in vitro in response to 5 mg/ml collagen. However, whole blood obtained after 25 hrs. of kistrin infusion (200 μg/hr) showed no aggregation.

Kistrin inhibited collagen-induced aggregation of guinea pig platelets in vitro in a dose-dependent-manner. At concentrations as low as 50 nM, kistrin was able to completely inhibit platelet aggregation in guinea pig whole blood.

Similarly, platelet aggregation was completely inhibited in animals receiving a kistrin infusion. Petechial and ecchymotic hemorrhages were observed on skin and internal organs during necropsy of the animals. This clotting failure is consistent with kistrin-induced platelet dysfunction. These findings indicate that kistrin binds to the fibrinogen receptor on guinea pig platelets and inhibits fibrinogen binding at concentrations comparable to human platelets.

Example 13: Effect of Kistrin on Platelet Count

No significant difference in platelet count was observed between treated and control animals. In kistrin-treated as well as in control animals, the platelet count remained between $484 \times 10^3/\mu l$ and $694 \times 10^3/\mu l$. These values are within the reported normal range for the guinea pig.

Example 14: Inhibition by Kistrin of Fibrinogen Incorporation into Platelets

The inhibition of fibrinogen endocytosis by kistrin was demonstrated by electrophoresis of platelet proteins. Biotinylated fibrinogen was injected into different guinea pigs with and without 5 mg of kistrin. Blood was collected at 24 hrs. and the platelets were purified therefrom, and the platelet proteins were solubilized, electrophoresed, Western blotted, and stained using avidin-horseradish peroxidase.

The technique used to detect biotinylated fibrinogen in platelets was extremely sensitive. Bands of less than 5 ng of labeled fibrinogen could be detected.

A dilution series of 5–250 ng of biotinylated fibrinogen was electrophoresed in an unreduced SDS-5% polyacrylamide gel, transferred to nitrocellulose and blotted with avidin horseradish peroxidase. Using a semi-quantitative Western assay, it was estimated that approximately 50 ng of injected biotinylated fibrinogen per $2 \times 10^7$ platelets were present 24 hrs. after infusion into control animals. Since the lower detection threshold is 5 ng, kistrin-treated animals had less than 5 ng of biotinylated fibrinogen per $2 \times 10^7$ platelets, because none could be detected. Thus, kistrin treatment of the animals reduced the biotinylated fibrinogen content of platelets to less than 10% of control.

Example 15: Lack of Inhibition of Other α-granule Proteins by Kistrin

This experiment determined whether the blockage of the $\alpha_{IIb}\beta_3$ receptor by kistrin affected endogenous α-granule proteins such as PF-4 and the vWF subunit synthesized by megakaryocytes. The protein content of platelets from control and kistrin-treated animals were analyzed by Western immunoblots for their PF-4 and the reduced (Mr 220,000) subunit of vWf. In the case of PF-4, $2 \times 10^7$ platelets were electrophoresed in unreduced 18% SDS polyacrylamide gels at 100 V, and transferred at 100 V for 1 hr. to 0.1 mm nitrocellulose. Rabbit anti-human PF-4, diluted 1:100 in 1 % gelatin was incubated with the filter for 1 hr. at room temperature (~20° C.), washed, incubated with goat anti-rabbit IgG-conjugated to biotin 1:500 for 1 hr., washed, then incubated with avidin-horseradish peroxidase (1:500) for 30 min. and washed. The reaction was terminated with 4 chloronapthol $+H_2O_2$. In the case of vWF, $2 \times 10^7$ platelets were electrophoresed in reduced 5% SDS polyacrylamide gels at 100 V, for 1 hr., transferred at 100 V for 1 hr. to 0.45 mm nitrocellulose, then incubated with rabbit anti-human vWf antibody diluted 1:500 in 1 % gelatin for 1 hr. The remainder of the procedure was as described above. There was no detectable difference in these two endogenously synthesized proteins in controls and in animals infused with kistrin.

Kistrin did not alter the levels of PF-4 and vWF synthesized by megakaryocytes but completely inhibited the appearance of biotinylated fibrinogen in platelets. This suggests that the effect of kistrin is primarily on the uptake of fibrinogen and not due to a generalized alteration of α-granule proteins. Furthermore, the albumin level in platelets in a guinea pig receiving kistrin was 10.1 fg/platelet whereas that in a control animal receiving saline was 9.2 fg/platelet. Thus, the endocytosis of albumin, an α-granule protein accumulated exclusively from endocytosis, also appears to be largely unchanged by kistrin. This result further confirms that the specific pathway for the uptake of fibrinogen is the site of kistrin activity.

Although endogenous vWf represents nearly all of that found in platelets, it is possible that a minor fraction of α-granule vWf is endocytosed from plasma via $\alpha_{IIb}\beta_3$ since vWF also binds to this receptor (Ruggeri, Z. M., et al., "Glanzmann Thrombasthenia. Deficient Binding of von Willebrand Factor to Thrombin-Stimulated Platelets", P.N.A.S. (USA) 79:6038–6041 (1982)), as well as to glycoprotein Ib (Coller, B. S., et al., "Studies with a Murine Monoclonal Antibody that Abolishes Ristocetin-Induced Binding of von Willebrand Factor to Platelets: Additional Evidence in Support of GP Ib as a Platelet Receptor for von Willebrand Factor", Blood. 61:99–110 (1983)). Western blotting is not sufficiently quantitative to exclude the possibility that kistrin inhibited the uptake of circulating vWf if it constituted a relatively small fraction of the total α-granule protein. An immunoreactive band, Mr=24,000, was seen in control but not in kistrin-treated animals.

Example 16: Electron Microscopic Localization of Kistrin in Platelets

To determine if the kistrin that binds to the platelet endocytic receptor is internalized and incorporated into the α-granules, the ultrastructural location of kistrin on platelets collected after 4 hrs. of infusion was determined. Since an anti-kistrin antibody was not available, kistrin was labeled with biotin and used to locate it in platelets. The platelets were found to contain endocytosed kistrin within α-granules and other organelles. Transmission electron micrographs showed the localization of kistrin in platelets obtained from a guinea pig given biotinylated kistrin for 4 hrs. in the form of a continuous infusion. Frozen thin sections of the platelets were stained for labeled kistrin using an anti-biotin antibody and an immunogold label that was enhanced with silver. There was marked variability in the amount and location of kistrin among platelets. Some platelets had only an occasional α-granule that contained kistrin. Frequently, labeling was closely associated with the granule membrane. Some labeling was also seen on the platelet plasma membrane. Kistrin was sometimes observed within organelles other than typical α-granules. Multiple kistrin-containing α-granules were seen in about 15% of the platelets.

Only about 60% of platelets were labeled for the presence of kistrin. Since the lifespan of a guinea pig platelet appears to be about 4 days, only a small percentage of platelets would be shed from bone marrow megakaryocytes during the 4 hrs. that the kistrin infusion lasted. Thus, it is likely that at least some of the kistrin was endocytosed by circulating platelets.

The present data show that even when a non-physiologic protein such as kistrin binds to the $\alpha_{IIb}\beta_3$ receptor, it is targeted to the α-granule.

Example 17: In Vivo Blocking of $\alpha_{IIb}\beta_3$ Receptor by Barbourin

Six Hartley guinea pigs, each weighing 500 gm, were used. Because disintegrins appear to have a short in vivo half life (Dennis, (1989), supra), barbourin was administered by continuous intravenous infusion in order to provide a sustained plasma level and maintain a continuous inhibition of the $\alpha_{IIb}\beta_3$ receptor. To study the effect of the $\alpha_{IIb}\beta_3$ blockade, barbourin (200 mg/hr) was infused for the duration of the experiment.

The effect on the endocytosis of fibrinogen or albumin by megakaryocytes of blockading the receptor was determined by i.v. administration of biotinylated fibrinogen (1 50 mg/animal) or biotinylated albumin (500 mg/animal). The controls consisted of sham-infused (saline instead of barbourin) animals injected with biotinylated fibrinogen and albumin. All animals were sacrificed at 24 hours and the bone marrow and blood platelets processed for immunohistochemical detection of biotinylated proteins as previously described (Handagama (1989), supra).

Example 18: Effect of Barbourin on Localization of Biotinylated Fibrinogen and Albumin The injected biotinylated fibrinogen or albumin was localized on plastic embedded marrow sections by staining with rabbit anti-biotin antibody (Enzo Biochem. Inc.,New York, N.Y.) according to a immunohistochemical technique described previously (Handagama (1989), supra). Staining with rabbit anti-vWF antibody (Dako Corp.,Carpinteria, Calif.) of bone marrow was carried out using the technique mentioned above, except that the biotin-sites in the tissue (injected biotinylated protein) were blocked using a Biotin-blocking kit (Vector Labs Inc., Burlingame, Calif.) prior to applying the primary antibodies. The biotinylated secondary antibody was from Vector Labs Inc. and the streptavidin reagents were from Zymed Labs, San Francisco. The controls were conducted by preincubating the tissue sections with biotin-blocking reagents in order to determine the specificity of staining for biotin in marrow sections. An additional control was conducted by staining marrow from an untreated guinea pig for the presence of biotin and substituting non-immune rabbit serum for the primary antibody.

Light photomicrographs of guinea pig bone marrow were prepared, embedded in plastic and stained for the localization of injected biotinylated proteins or endogenous von Willebrand factor (vWf) using the immuno-peroxidase technique. The brown peroxidase reaction product localized at antigenic sites. The tissue was counter-stained with hematoxylin and the megakaryocytes marked with an arrow head.

Megakaryocytesfrom animals injected biotinylated fibrinogen and receiving a continuous barbourin infusion did not stain. However, the injected biotinylated fibrinogen was endocytosed into megakaryocytes of sham-infused controls, and did stain. No difference in the endocytosis of biotinylated albumin by megakaryocytes was seen between barbourin-treated and control-treated animals. When the bone marrow from animals given biotinylated fibrinogen was stained for vWf, no difference in staining was observed between barbourin-treated and control-treated animals. The staining of sinus endothelial cells indicated the presence of biotinylated albumin which was injected in large amounts.

Example 19: Effect of Barbourin on Platelet Count and Aggregation

Platelet aggregation was performed using a whole blood aggregometer (Model 560 VS, Chrono-Log Corp., Havertown Pa.) with collagen as the agonist. The blood was collected by cardiac puncture into 3.8% sodium citrate. The aggregation assays were conducted at the termination of the experiments on blood drawn from animals continuously infused with barbourin or saline (control) for 24 hours. Platelet counting was conducted on samples obtained before treatment and 24 hrs. after the start of barbourin infusion using a Coulter counter (Coulter Corp., Hialiah, Fla.).

Collagen-induced platelet aggregation in whole blood was inhibited by the infusion of barbourin into a guinea pig. Platelets from sham-infused control animals aggregated rapidly in response to 5 mg/ml collagen, whereas platelets from animals infused for 24 hours with barbourin (200 mg/hr) showed no aggregation.

Example 20: Western Blot Analysis of Proteins in Barbourin-Treated Platelets Biotinylated fibrinogen was injected into different guinea pigs with or without 5 mg of barbourin. Blood was collected from both barbourin-treated and control animals 24 hrs. after the infusion of biotinylated fibrinogen, and the platelets were prepared as previously described (Handagama (1989), supra). The platelets were solubilized and electrophoresed in non-reduced 5% and 10% SDS polyacrylamide gels at 100 V, transferred for 1 hr. at 100 V onto 0.45 mm nitrocellulose filters, and; stained with avidin-horseradish peroxidase as previously described (Handagama (1989), supra).

A similar experiment was conducted injecting biotinylated albumin instead of biotinylated fibrinogen. The endocytosis of albumin was not affected by barbourin. The effect of barbourin on vWf was also determined using immunoblot analysis of platelets using the anti-vWf antibody mentioned above.

Example 21: Effect of Barbourin on Endocytosis of Fibrinogen or Albumin by Megakaryocytes Biotinylated fibrinogen was shown to be endocytosed by bone marrow megakaryocytes and incorporated into α-granules when administered to guinea pigs (Handagama (1989), supra). The infusion of barbourin virtually eliminated the uptake of labeled fibrinogen into megakaryocytes. Biotinylated albumin was endocytosed in similar amounts by megakaryocytes of barbourin-treated and control animals indicating that barbourin did not interfere with the endocytosis of albumin. Thus, barbourin appears to specifically inhibit the uptake of fibrinogen. No difference in the staining of megakaryocytes for endogenous vWF was seen between barbourin-treated and sham-infused controls, indicating that barbourin did not cause a generalized decrease of α-granule contents. The specificity of staining for the biotinylated protein was confirmed by the absence of staining in marrow sections preincubated with biotin-blocking reagents. Moreover, substituting marrow from untreated animals or non-immune serum for the primary antibody resulted in an absence of all staining (data not shown).

Example 22: Effect of Barbourin on Platelet Count and Platelet Aggregation

Compared to control platelets, collagen-induced aggregation was completely inhibited in animals receiving a barbourin infusion. This suggests that the infused dose of barbourin effectively occupied the $\alpha_{IIb}\beta_3$ sites on the platelets and inhibited fibrinogen binding.

No significant difference in platelet count was observed between treated and control animals. The platelet count remained between $441\times10^3$/ml and $558\times10^3$/ml. This is within the reported normal range for the guinea pig. The low and high counts were not associated with any particular treatment.

Example 23: Western Blot Analysis of Proteins in Barbourin-Treated Platelets In contrast to the sham-infused control, platelets from the barbourin-treated animal showed a complete absence of biotinylated fibrinogen. On the other hand, no difference between the platelets of barbourin-treated animals and controls was seen in the incorporation of biotinylated albumin. This is indicative of a specific endocytic mechanism for the uptake of fibrinogen from plasma into α-granules. No decrease in the endogenous vWf content of platelets was observed in animals infused with barbourin compared to controls (not illustrated) indicating that barbourin did not have a generalized effect on the contents of α-granules.

Example 24: Results and Conclusions

The endocytosis of biotinylated fibrinogen by megakaryocytes and platelets was prevented by the intravenous infusion of kistrin, an RGD-containing protein that inhibits fibrinogen binding to integrins. Kistrin appears to bind in vivo to megakaryocyte and platelet integrins that, in turn, bind fibrinogen. In this manner, kistrin prevents the delivery of fibrinogen to its storage site, the α-granule. The relocation of biotinylated kistrin was followed from its binding on the plasma membrane to the membranes surrounding the α-granules after internalization. Since fibrinogen, which comprises 10% of the protein of the α-granules is not synthesized by megakaryocytes (Handagama, P., et al., "Platelet Alpha-Granule Fibrinogen, Albumin and Immunoglobulin G are not Synthesized by Rat and Mouse Megakaryocytes", J. Clin. Invest. 86:1364–1368 (1990); Lange, W., et al., "Fibrinogen γ-chain mRNA is not Detected in Human Megakaryocytes", Blood. 78:20–25 (1991);and Louache, F., et al., "Fibrinogen is not Synthesized by Human Megakaryocytes", Blood. 77:311–316 (1991)), and is highly concentrated relative to its presence in plasma (George, J. N., "Immunoglobulin G: Its Significance for the Evaluation of Thrombocytopenia and for Understanding the Origin of α-Granule Protein", Blood 76:859–870 (1990)), it appears to be delivered to its storage site by receptor-mediated endocytosis. Furthermore, the endocytosis of fibrinogen appears to be mediated by integrins, since endocytosis can be prevented by an integrin antagonist.

The present results are in accord with the decrease in platelet-fibrinogen levels observed in humans and monkeys after the infusion of antibodies against the $\alpha_{IIb}\beta_3$ integrin receptor (Harrison, P., et al., "The Influence of Therapeutic Blockage of GP IIb-IIIa on Platelet α-Granule Fibrinogen", Blood. 76:458a (1990); Suzuki, M., et al., "Effect of Injected Antibody Against the Platelet Glycoprotein IIb-IIIa Complex on Monkey Platelet Fibrinogen", Thromb. Haemost. 67:578–581 (1992)).

The fibrinogen endocytosed by megakaryocytes is incorporated into α-granules, and the platelets are then able to secrete intact fibrinogen upon stimulation. Thus, the integrin-mediated endocytosis of fibrinogen in megakaryocytes and platelets and its incorporation into secretory granules most likely involves a previously unrecognized pathway. The present data show that even when a non-physiological protein such as kistrin binds to this receptor, it is targeted to the α-granule.

As discussed above, kistrin has been shown to bind $\alpha_{IIb}\beta_3$ and inhibit fibrinogen binding. Kistrin may, however, also bind to the vitronectin receptor ($\alpha_v\beta_3$), another fibrinogen-binding platelet integrin. Thus, $\alpha_{IIb}\beta_3$, $\alpha_v\beta_3$ or both are suitable candidates for mediating the endocytosis of fibrinogen into α-granules.

As already indicated, a variety of ligands, including fibrinogen, vWf, fibronectin, and thrombospondin, having the RGD recognition sequence bind $\alpha_{IIb}\beta_3$ on stimulated platelets. The fibrinogen molecule contains two RGD sequences both on the a chain and an additional $\alpha_{IIb}\beta_3$ binding site located at the C-terminus of the γ chain, which includes 12 amino acids but does not contain the RGD sequence. This dodecapeptide and RGD containing peptides compete with each other for binding to $\alpha_{IIb}\beta_3$. Thus, kistrin may inhibit both dodecapeptide- and RGD-mediated fibrinogen binding to $\alpha_{IIb}\beta_3$.

The present experiments show integrins acting as receptors for protein uptake into secretory granules. A somewhat similar function of integrins described recently involve the entry of certain microbial pathogens into host cells. Some bacteria appear to utilize the β1 integrin family of cell adhesion molecules as invasion receptors. Invasion, a 103 kD outer membrane protein, promotes the invasion of mammalian cells by bacteria such as certain strains of *Escherichia coli* and *Yersinia tuberculosis*. The specific binding of purified invasion to β1 chain paired to α chains 3,4,5 or 6 suggests that the attachment and entry into the bacteria expressing invasion requires these integrins. Other examples of integrin-mediated phagocytic uptake of microbes include *Legionella pneumophilia, Bordetella pertussis*, and the protozoan Leishmania.

The active cycling pool of the $\alpha_{IIb}\beta_3$ receptor in platelets, and its presence on the α-granule membrane was recently shown. However, the intra-granular storage pattern determined by immunoelectron microscopy shows fibrinogen to be randomly distributed in the matrix of α-granules except the nucleoid. This suggests that at least some of the fibrinogen molecules within the α-granules may dissociate from their membrane-bound receptor. The endocytosed kistrin that was incorporated into the α-granules showed a similar distribution. Thus, the kistrin molecules may have dissociated from their receptor(s) after reaching the α-granule.

Thus, the receptor that mediates fibrinogen endocytosis into α-granules has been shown to be an integrin. Kistrin, a member of the "disintegrin" family of RGD-containing peptides isolated from viper venoms has been shown to block the uptake of fibrinogen into megakaryocytes and platelet α-granules. It is possible that the effect of kistrin is mediated by its binding to $\alpha_{IIb}\beta_3$, the fibrinogen receptor on platelets. It has been shown, however, that kistrin also binds to several other RGD-dependent integrins on platelets including the $\alpha_v\beta_3$ vitronectin receptor, and the $\alpha_5\beta_{b1}$ fibronectin receptor. Therefore, it is also possible that the effect of kistrin on the endocytosis of fibrinogen is due to the inhibition of one of the other integrins in addition to, or rather than, $\alpha_{IIb}\beta_3$. The snake venom protein barbourin, contains the sequence lysine-glycine-aspartate (KGD) instead of RGD present in most of the other disintegrins. Barbourin has been shown to bind more specifically to $\alpha_{IIb}\beta_3$ than other disintegrins, including kistrin (Scarborough et al., supra).

The in vivo blockade of $\alpha_{IIb}\beta_3$ by infusion of the disintegrin peptide barbourin completely inhibited the appearance of biotinylated fibrinogen in megakaryocytes and platelets but did not effect the endocytosis of albumin nor did it alter the protein content of endogenously synthesized α-granule. The effect is thus mediated by inhibition of a specific mechanism involved in fibrinogen uptake and not by a generalized inhibition of endocytosis or alteration of α-granule contents. The integrin $\alpha_{IIb}\beta_3$ has been shown to be the primary receptor responsible for the endocytosis and entry of fibrinogen into the α-granule.

The present experimental data, along with information known in the art and referred to above, support the concept of $\alpha_{IIb}\beta_3$ as the primary receptor that mediates fibrinogen endocytosis.

Several other lines of evidence supporting this conclusion are listed below.

(a) In the genetic disorder Glanzmann thrombasthenia, in which $\alpha_{IIb}\beta_3$ is deficient or functionally abnormal, there is a deficiency of platelet fibrinogen.

(b) Platelet fibrinogen was shown to be decreased in humans and monkeys receiving monoclonal antibodies against $\alpha_{IIb}\beta_3$.

(c) $\alpha_{IIb}\beta_3$ is present on the α-granule membrane and it actively cycles in platelets.

(d) The variant fibrinogen γ', which lacks the $\alpha_{IIb}\beta_3$ RGD binding sequence, is not found in platelet α-granules even though it constitutes 10% of normal plasma fibrinogen.

(e) The platelets from patients with Paris I type dysfibrinogenemia, which do not bind normally to $\alpha_{IIb}\beta_3$, do not contain the abnormal fibrinogen, although 50% of the fibrinogen molecules in plasma have the defect.

These observations, when taken together with the present experimental data, show that $\alpha_{IIb}\beta_3$ is the primary receptor that mediates fibrinogen endocytosis. The possibility remains, however, that a small amount of fibrinogen may enter the α-granules via alternate receptors, i.e. $\alpha_v\beta_3$ and/or by fluid-phase endocytosis.

How $\alpha_{IIb}\beta_3$ serves as a receptor for fibrinogen is unclear. Fibrinogen binds to $\alpha_{IIb}\beta_3$ on intact platelets only after "activation". However, it has been shown that immobilized fibrinogen binds to $\alpha_{IIb}\beta_3$ without activation, and fibrinogen also binds to an integrin such as $\alpha_v\beta_3$, and may bind to "resting" $\alpha_{IIb}\beta_3$ receptors on the same or another cell. Similar mechanisms may be operative in vivo. A dimeric form of the dodecapeptide γ-chain sequences appear to be necessary for the incorporation of fibrinogen into α-granules, since fibrinogen-containing heterodimeric γgA and γ' molecules are absent in platelets. Thus, a "bridging" of two receptors by specific sequences of a divalent molecule may be required to elicit the endocytic response. The translocation of $\alpha_{IIb}\beta_3$ monoclonal antibodies or RGD or KGD peptides such as kistrin and barbourin into α-granules indicates that other ligands may also be endocytosed after binding to $\alpha_{IIb}\beta_3$.

The functional role of platelet integrins has been exclusively associated with their well established cell-cell and cell-matrix interactions. Thus, up to the present time, the sole function attributed to integrins such as $\alpha_{IIb}\beta_3$ was their role in platelet aggregation during formation of the hemostatic plug.

These experiments show a previously unrecognized function of integrins that comes into play during the development of cells of the platelet lineage, namely receptor-mediated endocytosis and storage of a major granule protein.

Example 25: Materials Used in Recombinant Methods

The following oligonucleotides were used in the construction of the vector carrying sequences encoding the urokinase/echistatin hybrid protein.

(a) 60 base per Human Urokinase Nucleotide
5' GATCAGAAGTCACACCAAGGAA-GAGAATGGCCTG (Seq. ID No. 1) 3' TCTTCAGT-GTGGTTCCTTCTCTTACCGGAC (Seq. ID No. 2)
GCCCTCTCTAGAACTAGTGCGGCCGC 3' (Seq. ID No. 3) CGGGAGAGATCTTGATCACGCCG-GCGCTAG 5' (Seq. ID No. 4)

(b) EE linker Oligonucleotide
5'CTAGAGAGGAAGAGGAATACATGCCTATGGAG (Seq. ID No. 5) 3' TCTCCTTCTCCTTATGTACG-GATACCTC (Seq. ID No. 6)
GGATCCTAGCCTCGAGGC 3' (Seq. ID No. 7) CCTAGGATCGGAGCTCCGCCGG 5' (Seq. ID No. 8)

(c) Echistatin Oligonucleotide
The complete sequence of echistatin was described by Gan et al. (Gan, Z.-R., et al., Gene 79:159–166(1989), and is incorporated herein by reference).

(d) pSPEcs Primer (Arg to Lys)
GTAAGCGCGCAAAGGGTGATGATCTC (Seq. ID No. 9) GAGATCATCACCCTTTGCGCGCTTAC (Seq. ID No. 10)

(e) The $pSVS_{cu}$-$PAA32_{kd}$DHFT expression vector is used to construct and carry the DNA encoding the urokinase/echistatin hybrid protein.

(f) The pZRG1 vector is used to carry the echistatin polynucleotide sequences during sequence mutation.

Example 26: Construction of Vectors

The $pSVS_{cu}$-$PA32_{kd}$DHFR vector is modified to remove a BamHI site. The pSVScuPA32kdDHFR expression vector is digested with μg BamHI restriction endonuclease and the digestion product is isolated by electrophoresis.

The 60 bp urokinase polynucleotide kinase is phosphorylated, annealed to the pSVScu-PA32kd(dBHI) DHFR expression vector and ligated with $T_4$ ligase. This results in the pSVScu-PA32kd(dBHI)60DHFR vector carrying the urokinase polynucleotide. The vector is then annealed to the EE oligonucleotide shown in example 25. pSVScu-PA32kd(dBHI)60DHFR is digested with a combination of XbaI and NotI restriction endonucleases, and annealed with kinase phosphorylated EE oligonucleotide at 95° C. and slowly cooled. The pSVScu-PA32kd(dBHI) 60DHFR vector is isolated by electrophoresis.

The pZRGI vector is modified by replacing EcoRI sites with BamHI and SalI sites. The vector is digested with EcoRI endonuclease and the product is amplified by polymerase chain reaction (PCR) using the AGCTGGATC-CGAATGCGAATCAGGTCC ATG primer (Seq. ID No. 11) at the N terminus, and the AGC TGTCGACTTAGG-TAGCTGGACCCTTGTG primer (Seq. ID No. 12) at the C terminus, to insert an N-terminal BamHI and C-terminal SalI site in place of the EcoRI ends. The pSP73 vector is isolated as described. above.

The pSP73 vector is digested with BamHI and SalI restriction endonucleases, and annealed to the kinase phosphorylated echistatin oligonucleotide and isolated as described above. The product is then ligated to produce the pSPEcs vector carrying the echistatin oligonucleotide.

The pSPEcs vector is amplified by PCR using a previously described technique (Jones, P. H., and Winistorfer, S. C., BioTechniques 12:1528 (1992)). The vector primers used are the following.

5' GAGAAAGGCGGACAGGTTCCG (Seq. ID No. 13).
5' CGGATACCTGTCCGCCTTTCTC (Seq. ID No. 14).

The mutoganizing primers used are provided in example 25.

The primer replaces the Arg with a Lys at amino acid 24 of the echistatin sequence described by Gan et al. (Gan, et al. (1989), supra), which is incorporated herein by reference. The pSPEcs(Lys) is digested with BamHI and SalI restriction endonucleases and the Lys-echistatin oligonucleotide is then isolated.

The pSVS$_{cu}$-PA32$_{kd}$(dBHI)60DHFR (+EE) is then digested with BamHI and XhoI restriction endonucleases. The mutated echistatin oligonucleotide is then kinase phosphorylated and annealed to the pSVS$_{cu}$-PA32kd(dBHI) 60DHFR (+EE). This vector is ligated with T$_4$ ligase. The resulting vector pSVLysEcs carries a 28 base pair urokinase encoding sequence adjacent to the EE polynucleotide linker, which is in turn flanked by the 51 base pair echistatin polynucleotide.

Example 27: Expression of Urokinase/Echistatin Hybrid Protein

The hybrid protein is isolated from Chinese hamster ovary (CHO) cells transfected with pSVLysEcS. The cells are grown in CHO-S-SFM medium (Life Technologies, Inc.) according to the method of Argerinos et al. (Argerinos, C. G., et al., Biotechnology 8:54–58 (1990)). The cells are lysed and their hybrid protein prepared according to the method of Booyse et al. (Booyse, F. M., et al., J. Biol. Chem. 259:7198 (1984); Koch, W., et al., Mol. & Cellular Biol. 6:1866–1874 (1988)). The hybrid protein is separated by affinity chromatography on a column of 5 ml benzamidine-sepharose and then, further purified by separation on a 5 ml sepharose column coupled with antibodies reactive to the Glu-Glu-Glu-Tyr-Met-Pro-Met-Glu polypeptide (EE).

Example 28: Biotinylation of Urokinase-Echistatin Hybrid Protein 5.0 mg of urokinase-echistatin hybrid protein, 2.5 mg/ml in 0.15 M NaCl/0.01 M NaPO4 pH 7.4 are incubated with biotinyl-ε-amino-caproic acid N-hydroxysuccinimide ester at a final concentration of 50 μg/ml at 0° C. for 3 hrs. The urokinase-echistatin hybrid protein is then dialyzed extensively against 0.1 5M NaCl/0.01 M NaPO4, pH 7.4, using 10,000 MW dialysis tubing from SPECTRA/POR.

Example 29: Fate of Urokinase-Echistatin in Megakaryocytes and Platelets

Biotinylated urokinase-echistatin is infused into guinea pigs overa 4 hr. period. The localization of the biotinylated urokinase-echistatin protein in megakaryocytes is determined on plastic embedded bone marrow sections prepared for light microscopy. The urokinase-echistatin present in platelets is localized by frozen thin section electron microscopy.

Example 30: Uptake of Urokinase-Echistatin by Megakaryocytes

The biotinylated urokinase-echistatin hybrid protein is localized on plastic embedded marrow sections by staining with streptavidin-peroxidase followed by biotinylated-peroxidase as described above.

Example 31: Urokinase Assay

The activity of the urokinase in the urokinase-echistatin hybrid protein is determined by quantitating the lysis of thrombin-stimulated fibrin clots in platelet-rich plasma with urokinase-echistatin hybrid protein. The assay is performed on blood drawn from animals continuously infused with urokinase-echistatin hybrid protein or saline (control) for 1 hr.

Example 32: Detection of Urokinase-Echistatin Fusion Protein in Megakaryocytes and Platelets The urokinase-echistatin hybrid protein is identified in megakaryocytes and platelets using Western immunoblots of solubilized protein.

Solubilized platelets and megakaryocytes are electrophoresed and transferred to Western immunoblots. The blots are reacted with antibody prepared against urokinase bound to the EE linker peptide described above. Bands are identified by labeled reacting anti-antibody.

Example 33: Localization of Urokinase-Echistatin Hybrid Protein in Platelets To determine if the urokinase-echistatin hybrid protein is endocytosed, biotinylated urokinase-echistatin hybrid protein is localized by electron microscopy on frozen thin sections. Platelets are fixed in 4% paraformaldehyde in 0.1 M phosphate buffer, pH 7.4, for 2 hrs. at 4° C. The platelets are then infiltrated overnight with 2.3 M sucrose, embedded in sucrose, frozen, stored in liquid nitrogen, and thin sections prepared. The biotinylated urokinase-echistatin hybrid protein is localized using rabbit anti-biotin antibody and a 1 nm gold probe conjugated to goat anti-rabbit IgG. The small probe is then amplified using silver chloride to facilitate detection (Stierhof et al. (1991), supra). Controls consisting of platelets from normal guinea pigs are prepared and stained identically.

Example 34: Effect of Urokinase/Echistatin Protein on Platelet Count

No significant difference is observed in the platelet counts between urokinase/echistatin-treated and control-treated animals. In urokinase/echistatin-treated as well as in control animals, platelet counts remain within a similar range. These values are within the reported normal range for the guinea pig.

Example 35: Electronmicroscopic Localization of Urokinase/Echistatin in Platelets To determine if the urokinase/echistatin hybrid protein that binds to the platelet endocytic receptor is internalized and incorporated into the α-granules, the ultrastructural localization of the urokinase/echistatin hybrid on platelets collected 4hrs. after infusion was determined. The urokinase/echistatin hybrid protein is labeled with biotin and the biotinylated protein thus localized in platelets. The hybrid protein is also localized with biotin labeled antibody binding to the EE linker peptide. The platelets are found to contain endocytosed urokinase/echistatin hybrid protein within the α-granules and other organelles. There is marked variability in the amount and location of the urokinase/echistatin hybrid protein among platelets. Some platelets only have an occasional α-granule that contains labeled urokinase/echistatin hybrid protein. Frequently, labeling is closely associated with the granule membrane, but sometimes it is also seen on the platelet plasma membrane. The presence of the urokinase/echistatin hybrid protein is sometimes also observed within organelles other than typical α-granules.

A large percentage of the platelets take up label showing the presence of the urokinase/echistatin hybrid protein. Since the lifespan of a guinea pig platelet appears to be about four days, only a small percentage of platelets are shed from bone marrow megakaryocytes during the 4 hrs. period of urokinase/echistatin hybrid protein infusion. Thus, it is likely that at least some of the urokinase/echistatin hybrid protein is endocytosed by circulating platelets.

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
       (A) LENGTH: 34 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

GATCAGAAGT CACACCAAGG AAGAGAATGG CCTG                                        34

(2) INFORMATION FOR SEQ ID NO:2:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

TCTTCAGTGT GGTTCCTTCT CTTACCGGAC                                             30

(2) INFORMATION FOR SEQ ID NO:3:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

GCCCTCTCTA GAACTAGTGC GGCCGC                                                 26

(2) INFORMATION FOR SEQ ID NO:4:

(i) SEQUENCE CHARACTERISTICS:
       (A) LENGTH: 30 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:4:

CGGGAGAGAT CTTGATCACG CCGGCGCTAG                                             30

(2) INFORMATION FOR SEQ ID NO:5:

(i) SEQUENCE CHARACTERISTICS:
       (A) LENGTH: 32 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:5:

CTAGAGAGGA AGAGGAATAC ATGCCTATGG AG        32

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TCTCCTTCTC CTTATGTACG GATACCTC        28

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GGATCCTAGC CTCGAGGC        18

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CCTAGGATCG GAGCTCCGCC GG        22

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GTAAGCGCGC AAAGGGTGAT GATCTC        26

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

-continued (xi) SEQUENCE DESCRIPTION: SEQ ID NO:10:

GAGATCATCA CCCTTTGCGC GCTTAC                                    26

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AGCTGGATCC GAATGCGAAT CAGGTCCATG                                30

(2) INFORMATION FOR SEQ ID NO:12:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

AGCTGTCGAC TTAGGTAGCT GGACCCTTGT G                              31

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GAGAAAGGCG GACAGGTTCC G                                         21

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CGGATACCTG TCCGCCTTTC TC                                        22

The invention now being fully described, it will be apparent to one of ordinary skill in the art that many changes and modifications can be made thereto without departing from the spirit or scope of the invention as set forth herein.

What is claimed as novel in Letters Patent of the United States is:

1. A therapeutic composition for in situ treatment of vascular injury, atherosclerosis or thrombosis by targeted delivery of a therapeutic compound to a site of vascular injury, said composition comprising the therapeutic compound conjugated with kistrin, wherein said therapeutic compound is an anti-atherosclerotic compound selected from the group consisting of an inhibitor of platelet-derived growth factor, an inhibitor of monocyte chemotaxis factor, endothelial growth factor and superoxide, an antithrombotic agent selected from the group consisting of urokinase, tissue plasminogen activator, hirudin, and heparin, or a cardiovascular agent selected from the group consisting of a vascular endothelial cell growth factor, platelet derived endothelial growth factor and an inhibitor of atherosclerotic plaque development, present in a therapeutically effective amount;

wherein said composition binds to and is uptaken by megakaryocytes or platelets;

wherein upon platelets activation, said composition is transported and delivered to the site of vascular injury by activated platelets; and wherein upon delivery of the composition to the site of vascular injury, the therapeutic compound treats vascular injury, atherosclerosis or thrombosis in situ.

2. The composition of claim 1 wherein the uptake of the composition by the platelets or megakaryocytes is in vitro or in vivo.

3. The composition of claim 2, wherein said therapeutic compound conjugated to kistrin is present in an amount sufficient to provide a patient with about 0.001 to 100 mg/kg body weight/dose.

4. The composition of claim 3, wherein said therapeutic compound is present in an amount sufficient to provide a patient with about 0.01 to 10 mg/kg body weight/dose.

* * * * *